United States Patent
Marziliano et al.

(10) Patent No.: US 9,364,160 B2
(45) Date of Patent: Jun. 14, 2016

(54) SYSTEMS AND METHODS FOR ECG MONITORING

(71) Applicant: QUALCOMM Incorporated, San Diego, CA (US)

(72) Inventors: Pina Marziliano, Singapore (SG); Amrish Nair, Singapore (SG)

(73) Assignee: QUALCOMM Incorporated, San Diego, CA (US)

( * ) Notice: Subject to any disclaimer, the term of this patent is extended or adjusted under 35 U.S.C. 154(b) by 97 days.

(21) Appl. No.: 13/797,889

(22) Filed: Mar. 12, 2013

(65) Prior Publication Data

US 2013/0261482 A1    Oct. 3, 2013

Related U.S. Application Data

(60) Provisional application No. 61/616,890, filed on Mar. 28, 2012.

(51) Int. Cl.
*A61B 5/0452* (2006.01)
*A61B 5/00* (2006.01)
*A61B 5/04* (2006.01)

(52) U.S. Cl.
CPC ............ *A61B 5/0452* (2013.01); *A61B 5/04012* (2013.01); *A61B 5/726* (2013.01); *A61B 5/7207* (2013.01)

(58) Field of Classification Search
CPC ...................................................... A61B 5/0425
USPC .................................................. 600/509, 521
See application file for complete search history.

(56) References Cited

U.S. PATENT DOCUMENTS

| 7,672,717 | B1 | 3/2010 | Zikov et al. |
| 7,774,063 | B2 | 8/2010 | Ghanem et al. |
| 8,073,218 | B2 | 12/2011 | Toth et al. |
| 2003/0185408 | A1 | 10/2003 | Causevic et al. |
| 2008/0167567 | A1 | 7/2008 | Bashour et al. |

(Continued)

FOREIGN PATENT DOCUMENTS

CN         102274020 A       12/2011

OTHER PUBLICATIONS

Chouakri S. A., et al., "Wavelet Denoising of the Electrocardiogram Signal Based on the Corrupted Noise Estimation," Computers in Cardiology, 2005, vol. 32, pp. 1021-1024.

(Continued)

*Primary Examiner* — Alyssa M Alter
(74) *Attorney, Agent, or Firm* — Knobbe, Martens, Olson & Bear LLP; Thomas Arno

(57) ABSTRACT

A method, system, apparatus and device for processing an ECG signal to remove or reduce noise from the ECG signal attributable to EMG and/or motion artifacts. The novel algorithm common to all aspects of the device can include wavelet decomposing an ECG signal to produce a set of approximation coefficients and a plurality of sets of detail coefficients, locally fitting subsets of the set of approximation coefficients to second order polynomials, adjusting the set of approximation coefficients by the locally fitted second order polynomials, setting some of the detail coefficients to zero, and reconstructing an ECG signal with reduced noise based on the modified set of approximation coefficients and the modified plurality of sets of detail coefficients.

33 Claims, 12 Drawing Sheets

(56) References Cited

U.S. PATENT DOCUMENTS

2010/0074482 A1* 3/2010 Toth et al. .................. 382/128
2011/0098583 A1* 4/2011 Pandia et al. ................ 600/508
2012/0123232 A1 5/2012 Najarian et al.

OTHER PUBLICATIONS

Chouhan V. S., et al., "Total Removal of Baseline Drift from ECG Signal," Proceedings of the International Conference on Computing: Theory and Applications (ICCTA'07), IEEE Computer Society, 2007, pp. 1-4.
Cleveland W. S., et al., "Robust Locally Weighted Regression and Smoothing Scatterplots," Journal of the American Statistical Association, Dec. 1979, vol. 74 (368), pp. 829-836.
Comon P. "Independent Component Analysis, A New Concept?," Signal Processing, 1994, vol. 36, pp. 287-314.
Donoho D. L., "De-Noising by Soft-Thresholding," IEEE Transactions on Information Theory, May 1995, vol. 41 (3), pp. 613-627.
Irino T. et al., "Signal Reconstruction from Modified Auditory Wavelet Transform," IEEE Transactions on Signal Processing, Dec. 1993, vol. 41 (12), pp. 3549-3554.
Jeong D. U., et al., "Development of a Technique for Cancelling Motion Artifact in Ambulatory ECG Monitoring System," Third 2008 International Conference on Convergence and Hybrid Information Technology, 2008 IEEE Computer Society, pp. 954-961.
Mallat S. G., et al., "A Theory for Multiresolution Signal Decomposition: The Wavelet Representation," IEEE Transaction on Pattern and Machine Intelligence, Jul. 1989, vol. 11 (7), pp. 674-693.
Mithun P. et al., "A Wavelet Based Technique for Suppression of EMG Noise and Motion Artifact in Ambulatory ECG," 33rd Annual International Conference of the IEEE EMBS Boston, Massachusetts USA, Aug. 30-Sep. 3, 2011, pp. 7087-7090.
Sornmo L. et al., "The Electrocardiogram, ECG Signal Processing, ECG Signal Processing: Heart Rate Variability," Bio Electrical Signal, 2005, Chapter 6, 7, 8, pp. 411-627. (uploaded in 2 parts).
Erçelebi, E: "Electrocardiogram signals de-noising using lifting-based discrete wavelet transform", Computers in Biology and Medicine, vol. 34. No. 6, Sep. 1, 2004, pp. 479-493, XP055063232, ISSN: 0010-4825, DOI: 10.1016/S0010-4825 (03) 00090-8.
International Search Report and Written Opinion—PCT/US2013/032109—ISA/EPO—May 29, 2013.
Dong H., et al., "Adaptive ECG De-noising Method Based on Stationary Wavelet Transform," Journal of Chinese Medical Instrumentation, Dec. 31, 2009 vol. 33(3), pp. 163-166.
Ren J., et al., "Methods of Removing ECG Baseline Drift Noise Based on Wavelet Transform Coefficients," Medical Equipment, Nov. 30, 2010, vol. 31(11), pp. 24-26.

* cited by examiner

SYSTEMS AND METHODS FOR ECG MONITORING

CROSS-REFERENCE TO RELATED APPLICATIONS

This application claims priority to U.S. Provisional Application No. 61/616,890 filed Mar. 28, 2012, which is hereby expressly incorporated in its entirety by reference herein.

FIELD

This disclosure relates to ECG monitoring and, more specifically, systems, methods and devices for processing an ECG signal to reduce noise in the signal.

BACKGROUND

Electrocardiograms (ECG) are electrical signals representing the impulses generated by the heart. The ECG signal and waveform is characterized by the P, QRS, and T waves, as seen in FIG. 1, produced during the atrial and ventricular contraction and relaxation of the heart muscle. FIG. 1 illustrates an example of a typical ECG signal 10, relatively free of any corruption or noise. ECG signal 10 demonstrates the characteristic P wave 12, Q wave 14, R wave 16, S wave 18, and T wave 20 features. ECG signals can be acquired using electrodes mounted to the skin of the subject in an area external to the heart. These electrodes can be affixed to the skin using adhesive on one surface of the electrodes. The electrodes can then acquire a signal from the electrical activity in and around the heart. The terms "ECG signal" and "signal" can refer to the analog output of ECG electrodes, as well as a processed or unprocessed sampled data points, e.g., sampled data points produced using an A/D converter. The analog signal and/or sampled data points may be filtered. The signal can then be further processed, stored, and/or transmitted or routed to a device configured to display the signal.

Artifacts, which include powerline interference, motion artifacts and electromyogram (EMG) signals, corrupt the ECG signal with "noise" and affect the performance of feature detection algorithms. It also affects accurate diagnosis by clinicians. Motion and EMG artifacts are frequent occurrences due to the movement of the test subject and electrical activity of other muscles near the heart. Corrupted ECG signals (e.g., ECG signals with motion and EMG artifacts) can be seen in FIGS. 2 and 3. Long period noise in a corrupted ECG signal, most notable in FIG. 2, is typically caused by subject motion and is referred to as a motion artifact. Higher frequency distortion shown in both FIGS. 2 and 3 in the corrupted ECG signal can be caused by the electrical activity of muscles surrounding or near to the heart. This type of distortion is referred to as EMG artifacts.

SUMMARY

The systems, methods and devices of the invention each have several aspects, no single one of which is solely responsible for its desirable attributes. Without limiting the scope of this invention as expressed by the claims which follow, some features will now be discussed briefly. After considering this discussion, and particularly after reading the section entitled "Detailed Description," one will understand how the features of this invention provide advantages that include reducing noise in an ECG signal attributable to subject motion and non-cardiac muscle activity.

In one aspect, a method for processing an ECG signal to reduce noise in the ECG signal is provided. The method includes wavelet decomposing an ECG signal containing artifacts, producing a set of approximation coefficients and a plurality of sets of detail coefficients. The approximation coefficients may be modified, removing motion artifacts. The approximation coefficients may be modified by first locally fitting adjacent subsets of the approximation coefficients to second order polynomials. After the approximation coefficients have been locally fitted to second order polynomials, the original set of approximation coefficients can be adjusted by the locally fitted second order polynomials by subtracting the second order polynomials from the corresponding approximation coefficients, resulting in a set of modified approximation coefficients. The detail coefficients may be thresholded to produce a plurality of sets of modified detail coefficients that can be used to remove EMG artifacts from the ECG signal. The thresholding may be position thresholding, and may be performed by setting some of the detail coefficients to zero based at least in part on the position of the detail coefficients with respect to an R wave of the ECG signal. In another implementation, the method further includes reconstructing the ECG signal from the modified approximation coefficients and thresholded detail coefficients, resulting in an ECG signal with reduced noise compared to the original ECG signal.

In another aspect, a system or apparatus for processing an ECG signal to reduce noise in the ECG signal is provided. The system or apparatus includes a processor configured to wavelet decompose an ECG signal containing noise, producing a set of approximation coefficients and a plurality of sets of detail coefficients. The processor is further configured to modify the approximation and/or detail coefficients. In another implementation, the processor can be further configured to reconstruct the ECG signal from the modified approximation coefficients and thresholded (e.g., modified) detail coefficients, resulting in an ECG signal with reduced noise compared to the original ECG signal. In yet another implementation, the system or apparatus further includes ECG electrodes, an A/D converter, and an antenna configured for mounting on the body of a subject.

In another aspect, a device for processing an ECG signal to reduce noise in the ECG signal is provided. The device includes a means for wavelet decomposing an ECG signal to produce a set of approximation coefficients and a plurality of sets of detail coefficients, modifying the set of approximation coefficients, and thresholding the detail coefficients. In one implementation, the device can further include a means for reconstructing the ECG signal from the modified approximation coefficients and thresholded (e.g., modified) detail coefficients.

The methods, systems and devices described in this disclosure may be implemented in hardware, software, firmware, or any combination thereof. If implemented in hardware, an apparatus may be realized as an integrated circuit, a processor, discrete logic, or any combination thereof. If implemented in software, the software may be executed in one or more processors, such as a microprocessor, application specific integrated circuit (ASIC), field programmable gate array (FPGA), or digital signal processor (DSP). The software that executes the methods, systems and devices may be initially stored in a computer-readable medium and loaded and executed in the processor.

Accordingly, this disclosure also contemplates a computer-readable storage medium comprising instructions that upon execution in a processor cause the processor to upon receiving an ECG signal, wavelet decompose the ECG signal to produce a set of approximation coefficients and a plurality of sets of detail coefficients, modify the set of approximation coefficients, and threshold the detail coefficients, reducing the noise in the ECG signal.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Novel methods and systems described herein are concerned with processing an ECG signal to reduce noise in the ECG signal. According to one implementation, a method for processing an ECG signal is provided. The method includes wavelet decomposing the ECG signal to produce a set of approximation coefficients and a plurality of sets of detail coefficients, and modifying the approximation and/or detail coefficients. In some implementations, the method further includes reconstructing the ECG signal from the modified approximation coefficients and/or modified (e.g., position thresholded) detail coefficients. As described further below, implementations of these modifications are very effective in reducing common noise sources in ECG signals.

Wavelet decomposition involves approximating a signal at progressively lower resolutions, with the difference in successive approximations each defining a detail signal. Wavelet decomposition produces a set of approximation coefficients and a plurality of sets of detail coefficients. Decomposition to the $n^{th}$ order produces $n^{th}$ level approximation coefficients, $A_n$, and a plurality of sets of detail coefficients $D_1$-$D_n$. The approximation coefficients produced represent the value of approximation functions (e.g., the approximated signal after decomposing) at discrete points. The detail coefficients represent the difference of the value of successive approximation functions at discrete points. Wavelet decomposition is described by Mallat, S., "A Theory for Multiresolution Signal Decomposition: The Wavelet Representation," *IEEE Trans. Pattern Anal. Mach. Intell.*, vol. 11, pp. 674-693, July 1989, the entire content of which is incorporated herein by reference. The general method of wavelet decomposition is well known, but the methods of coefficient processing described below have not been previously performed.

Figure 4:
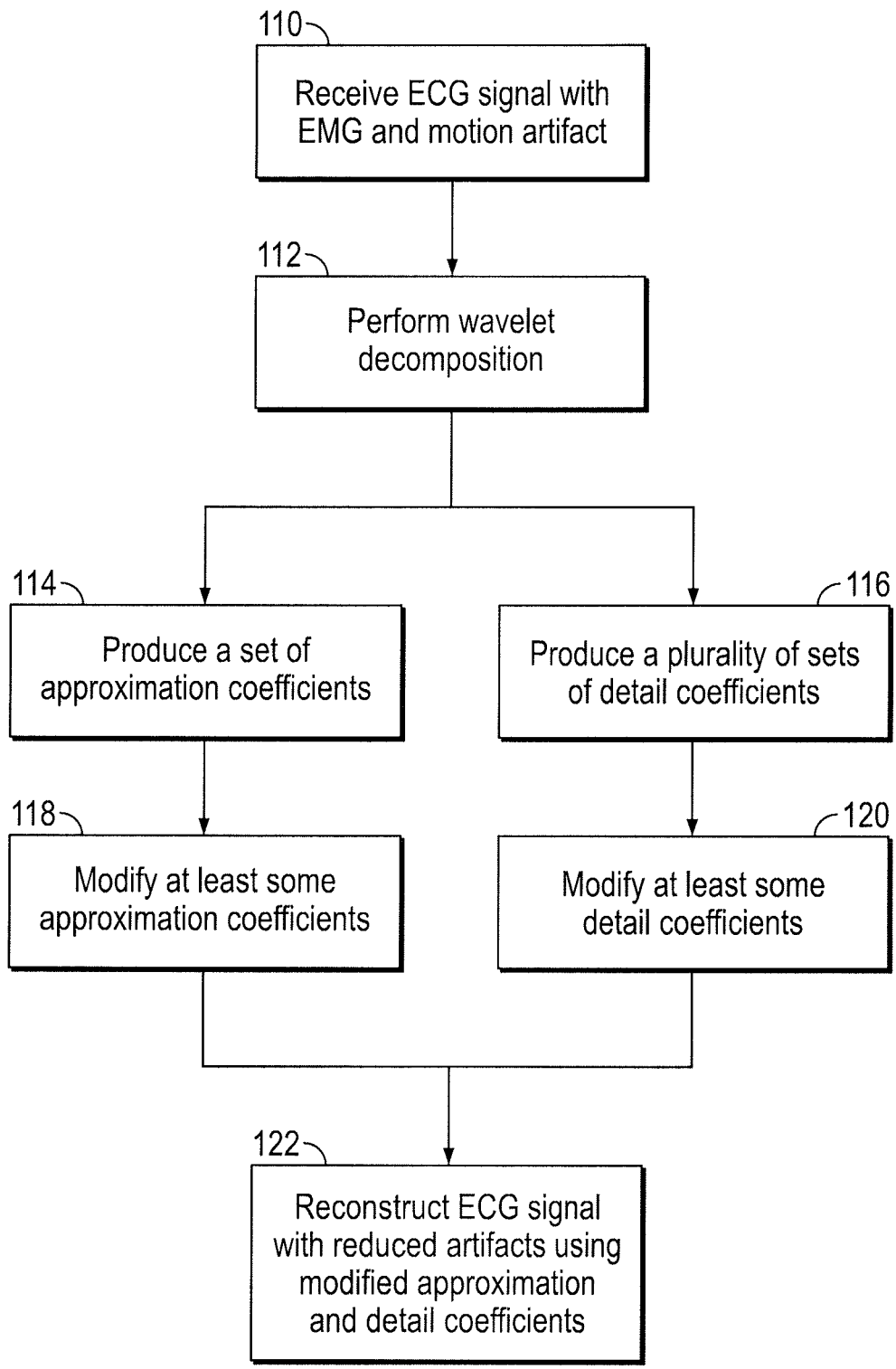
FIG. 4 show a process flow diagram for one implementation of a method for processing an ECG signal to remove or reduce noise caused by EMG and/or motion artifacts.

FIG. 4 shows a process flow diagram for one implementation of a method of processing an ECG signal to remove or reduce noise from the ECG signal. At block 110, an ECG signal, which may have at least an EMG and/or a motion artifact, is received. At block 112, wavelet decomposition is performed on the ECG signal received at block 110. Wavelet decomposition of block 112 produces a set of approximation coefficients, represented at block 114, and a plurality of sets of detail coefficients, represented at block 116. Blocks 114 and 116 are not separate operations, but are the result of the wavelet decomposition of block 112. The approximation coefficients of block 114 represent the value of the last approximation function (e.g., the approximated signal after decomposing) determined in block 112 at discrete points. The detail coefficients of block 116 represent the difference between successive approximation functions at discrete points. If the approximation and detail coefficients of blocks 114 and 116 are not modified, substantially the original ECG signal received at block 112 can be reconstructed from these coefficients.

At block 118, at least some of the approximation coefficients from block 114 are modified. In some implementations, the modification at block 118 reduces the average excursion of the approximation coefficients from the baseline. Preferably, the modification at block 118 can include reducing the average excursion from the baseline predominantly for excursions having a time scale longer than the R waves present in the data set. In some implementations, approximation coefficients modified in this way can be used to reconstruct an ECG signal at block 122 with reduced motion artifacts compared to the original ECG signal received at block 110. One suitable algorithm is described below with reference to FIG. 5.

At block 120, at least some of the detail coefficients from block 116 are modified, producing a plurality of modified detail coefficients. One well-known form of thresholding to reduce noise in a signal is "magnitude thresholding" in which detail coefficients of a wavelet decomposition of a signal are thresholded (e.g., set to zero) based at least in part on their magnitude (e.g., based on whether the detail coefficient has a magnitude greater than or less than the threshold magnitude). Although this technique may also be used to modify some detail coefficients in the context of the methods described herein, it has been found that noise reduction in an ECG signal is advantageously accomplished using a method referenced herein as "position thresholding," which involves modifying some detail coefficients based at least in part on their position in time within a set of detail coefficients. As described in more detail below with reference to FIG. 6, the position used for determining modifications may be relative to the position of an R wave in the signal. In some implementations, detail coefficients more than a predetermined distance from an R wave are set to zero, while detail coefficients less than or equal to a predetermined distance from the R wave are left unchanged. Additionally, in some implementations, all detail coefficients of lower order sets of detail coefficients, e.g., $D_1$, $D_2$ and/or $D_3$, can be set to zero. One specific implementation of this modification operation is discussed below in more detail. The plurality of sets of detail coefficients after some detail coefficients have modified (for example, either by setting entire sets of detail coefficients to zero, or by position thresholding) constitute the modified detail coefficients. In some implementations, the modified detail coefficients can be used to reconstruct an ECG signal at block 122 with reduced EMG artifacts, compared to the original ECG signal received at block 110.

At block 122, an ECG signal with reduced artifacts is reconstructed using approximation coefficients and detail coefficients, of which at least some of the approximation coefficients and/or detail coefficients have been modified. In some implementations, an ECG signal can be reconstructed using unmodified approximation coefficients (e.g., the approximation coefficients substantially as from block 114), and detail coefficients of which at least some of the detail coefficients have been set to zero according to block 120. In some implementations, an ECG signal can be reconstructed using unmodified detail coefficients (e.g., the detail coefficients substantially as from block 116), and approximation coefficients of which at least some of the approximation coefficients have been modified according to block 118. The ECG signal reconstructed at block 122 can have reduced or removed motion and/or EMG artifacts.

Figure 1:
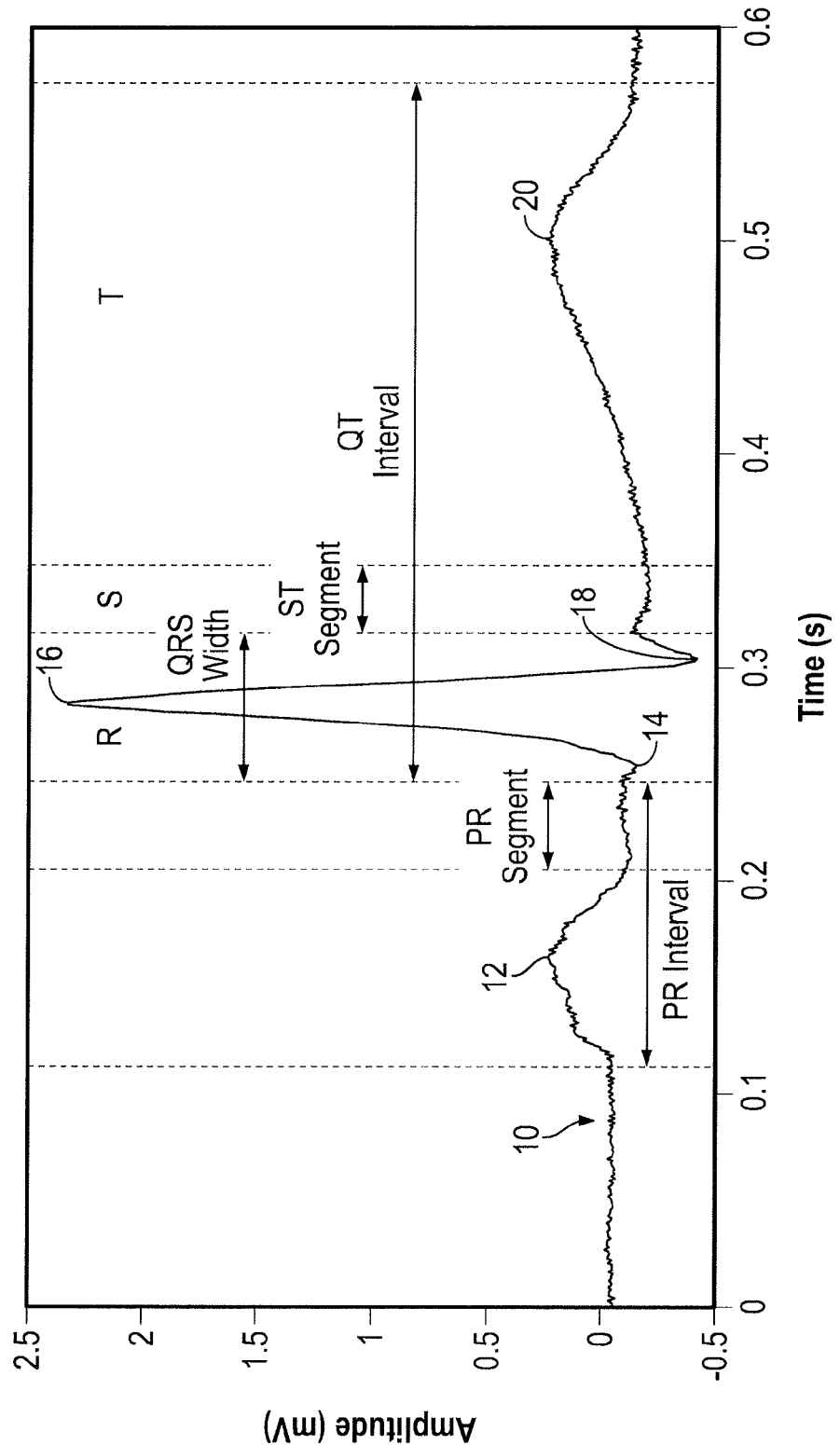
FIG. 1 shows an example of a typical ECG signal or waveform having characteristic P, QRS and T waves.
Figure 2:
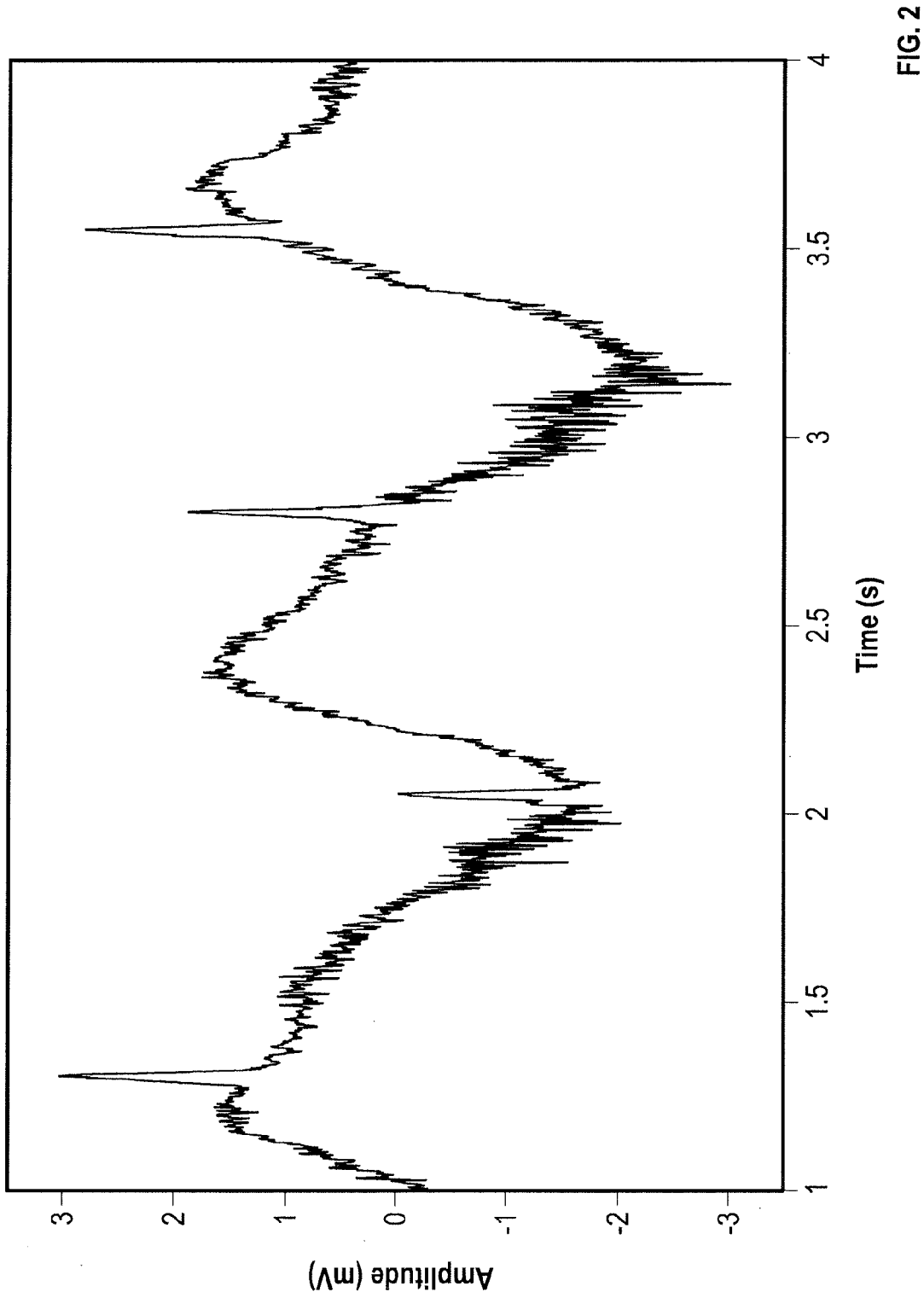
FIG. 2 shows an example of an ECG signal corrupted by EMG and motion artifacts.
Figure 5:
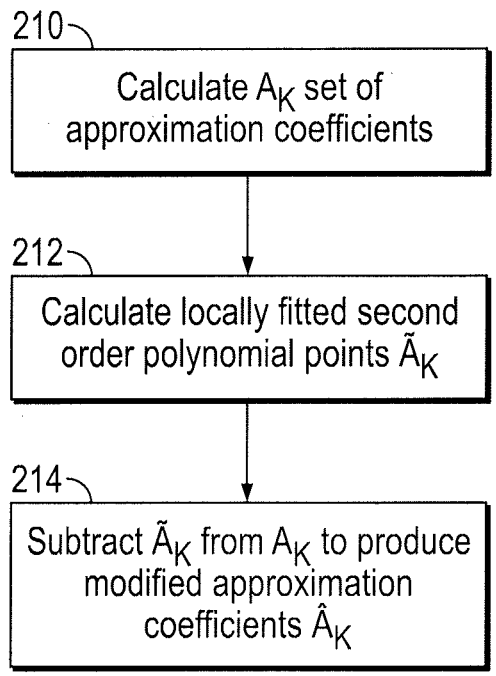
FIG. 5 shows a process flow diagram for one implementation of a method of modifying approximation coefficients.

FIG. 5 illustrates a process flow diagram for one implementation of a method of modifying at least some of the approximation coefficients. At block 210, a set of approximation coefficients $A_K$ is calculated from an ECG signal, where K can represent the order of decomposition used to calculate the approximation coefficients. At block 212, second order polynomials locally fitted to the set of approximation coefficients $A_K$ are calculated, producing a set of locally fitted points $\tilde{A}_K$ which reside on the fitted polynomial. The local fitting can be done using a locally weighted method such that the locally fitted points $\tilde{A}_K$ are generally fitted to the features of the motion artifact (as shown in FIG. 2), with little contribution from the prominent wave features (e.g., the PQRST waves) of the ECG signal (as shown in FIG. 1). At block 214, each computed $\tilde{A}_K$ is subtracted from its corresponding original $A_K$ to produce a set of modified approximation coefficients, $\hat{A}_K$. In some implementations, the set of modified approximation coefficients $\hat{A}_K$ calculated at block 214 can be used to reconstruct an ECG signal with a reduced or removed motion artifact. It will be appreciated that the method and any combination of operations of the method described above can be performed substantially in real time, e.g., as an ECG signal is acquired from a subject.

In some implementations, the local fitting of block 212 can be achieved using a locally weighted scatterplot smoothing (LOWESS) algorithm, which is described in Cleveland, W., "Robust Locally Weighted Regression and Smoothing Scatterplots," *Journal of the American Statistical Association*, vol. 74, pp. 829-836, December 1979, the entire content of which is incorporated herein by reference. In some implementations, polynomials are locally fitted to a subset of approximation coefficients, with the subset defined by an approximation coefficient from the set $A_K$ and a predetermined number of approximation coefficients immediately adjacent (e.g., a predetermined number of coefficients before and after the approximation coefficient). The subset of approximation coefficients used for local fitting defines a time period span for local fitting. The time period span to use for local fitting (e.g., the number of approximation coefficients to use as a segment for local fitting) should be relatively long compared to ECG waveform but relatively short compared to the motion artifact, so as to minimize the effect of the ECG waveform features on the fitting. In some embodiments, for example, a time period span of approximately 100-500 ms (e.g., a subset of approximation coefficients representing 100-500 ms of signal data) may be used for locally fitting subsets of approximation coefficients, with about 200 ms having been found suitable in some implementations.

The relative weight ("proximity weight") of each coefficient within the subset for fitting to a polynomial may be based at least in part on the proximity of the coefficient to the center of the subset of coefficients (e.g., based at least in part on a coefficient's distance from the center point of the subset of approximation coefficients), wherein coefficients closer to the center are accorded greater weight in the fitting. In some implementations, after a subset of approximation coefficients is locally fit to a second order polynomial ("first locally fit polynomial"), a new weight value ("residual weight") is accorded to each approximation coefficient in the subset based on the distance between the approximation coefficient and the corresponding point on the first locally fit polynomial, wherein coefficients closer to the first locally fit polynomial are accorded greater weight. Based at least in part on this residual weight for each coefficient within the subset, the subset of coefficients is again locally fit to a second order polynomial ("second locally fit polynomial"). Using this residual weighting for the fit suppresses the contribution to the fit of the desired ECG signal, forcing the fit to follow the longer period motion artifacts closely. In some implementations, this algorithm may be iterated more than once to calculate a final locally fit polynomial for each subset. Preferably, this algorithm is iterated twice to calculate a final locally fit polynomial for each subset. In some implementations, this algorithm is performed for each approximation coefficient in the set of approximation coefficients $A_K$ (e.g., a subset is defined and locally fit using this algorithm for each approximation coefficient within $A_K$). Each second order polynomial point in the set of $\tilde{A}_K$ may be determined by the value of the final locally fit polynomial for the subset centered on the corresponding point from the original set of approximation coefficients $A_K$. In some implementations, the set of modified approximation coefficients $\hat{A}_K$ are produced by adjusting the original set of approximation coefficients $A_K$ by the set of second order polynomial points $\tilde{A}_K$ by subtracting the set of second order polynomial points $\tilde{A}_K$ from the original set of approximation coefficients $A_K$. The set of modified approximation coefficients can be used to reconstruct an ECG signal with reduced motion artifacts.

Figure 6:
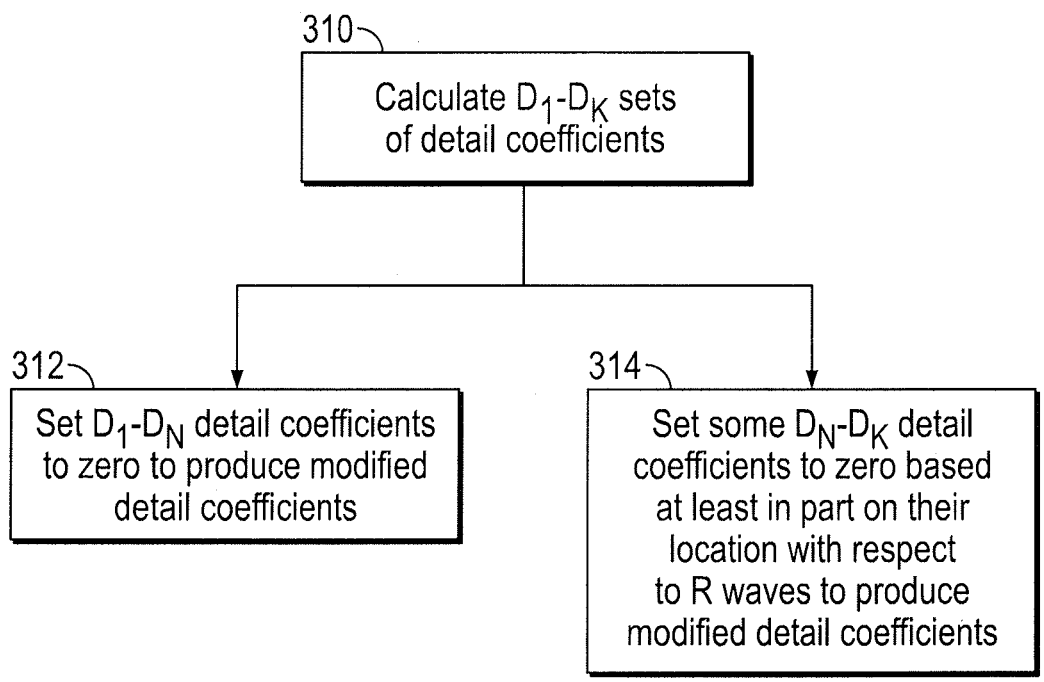
FIG. 6 shows a process flow diagram for one implementation of a method of modifying detail coefficients by setting at least some of the detail coefficients to zero.

FIG. 6 illustrates a process flow diagram for one implementation of a method of modifying the detail coefficients by setting at least some of the detail coefficients to zero. At block 310, $D_1$-$D_K$ sets of detail coefficients are calculated from an ECG signal, where K can represent the order of decomposition used to calculate the detail coefficients. At block 312, $D_1$-$D_N$ sets of detail coefficients can be set to zero. Depending on the sampling frequency used to obtain the ECG signal, the lower level sets of detail coefficients (e.g., $D_1$, $D_2$ and $D_3$) may not store significant information pertaining to the ECG waveform. Therefore, in some implementations, depending on the sampling frequency and/or other factors, $D_1$-$D_N$ sets of detail coefficients can be set to zero without losing any significant information pertaining to the ECG waveform. At block 314, some of the detail coefficients of sets $D_{N+1}$-$D_K$ can set to zero based at least in part on their position relative to the position of an R wave (e.g. an R "peak"). The sets of detail coefficients with at least some detail coefficients set to zero in blocks 312 and/or 314 comprise the sets of modified detail coefficients. The sets of modified detail coefficients can be used to reconstruct an ECG signal without EMG artifacts.

In some implementations, some detail coefficients are set to zero in block 314 using position thresholding, wherein detail coefficients that are more than a predetermined distance from an R wave peak are set to zero, and detail coefficients less than or equal to the predetermined distance are left unchanged. For example, for a set of detail coefficients $D_K$ and an R wave location $R_K[i]$ (where i is an index identifying each separate R wave in the time period spanned by the signal being processed), all detail coefficients of $D_K$ that are 4 $D_K$ data points or less away from $R_K[i]$ are unmodified, while all detail coefficients more than 4 data points away from $R_K[i]$ are set to zero. In some implementations, the distance at which to position threshold (e.g., the number of data points away from R used in the modification block 314) the detail coefficients can be derived based at least in part on the maximum period of the ECG waveform and the width of the ECG in the sets of detail coefficients to be thresholded. This distance can also vary based at least in part on the sampling frequency of the ECG signal from which the detail coefficients were calculated. In some implementations, this distance can be determined experimentally. The distance (e.g., number of points) to use as the position threshold may differ for different level sets of detail coefficients (e.g., a threshold of 4 points for $D_5$ coefficients and a threshold of 3 points for $D_4$ coefficients). The plurality of sets of detail coefficients after some detail coefficients have been set to zero (either by setting entire sets of detail coefficients to zero in block 312, or by position thresholding in block 314) constitute the sets of modified detail coefficients. It will be appreciated that blocks 312 and 314 can be performed independently of one another and need not both be performed in order to produce modified detail coefficients. In some implementations, the sets of modified detail coefficients can be used to reconstruct an ECG signal with reduced or removed EMG artifacts. It will be appreciated that the method and any combination of operations of the method described above can be performed substantially in real time.

Figure 7:
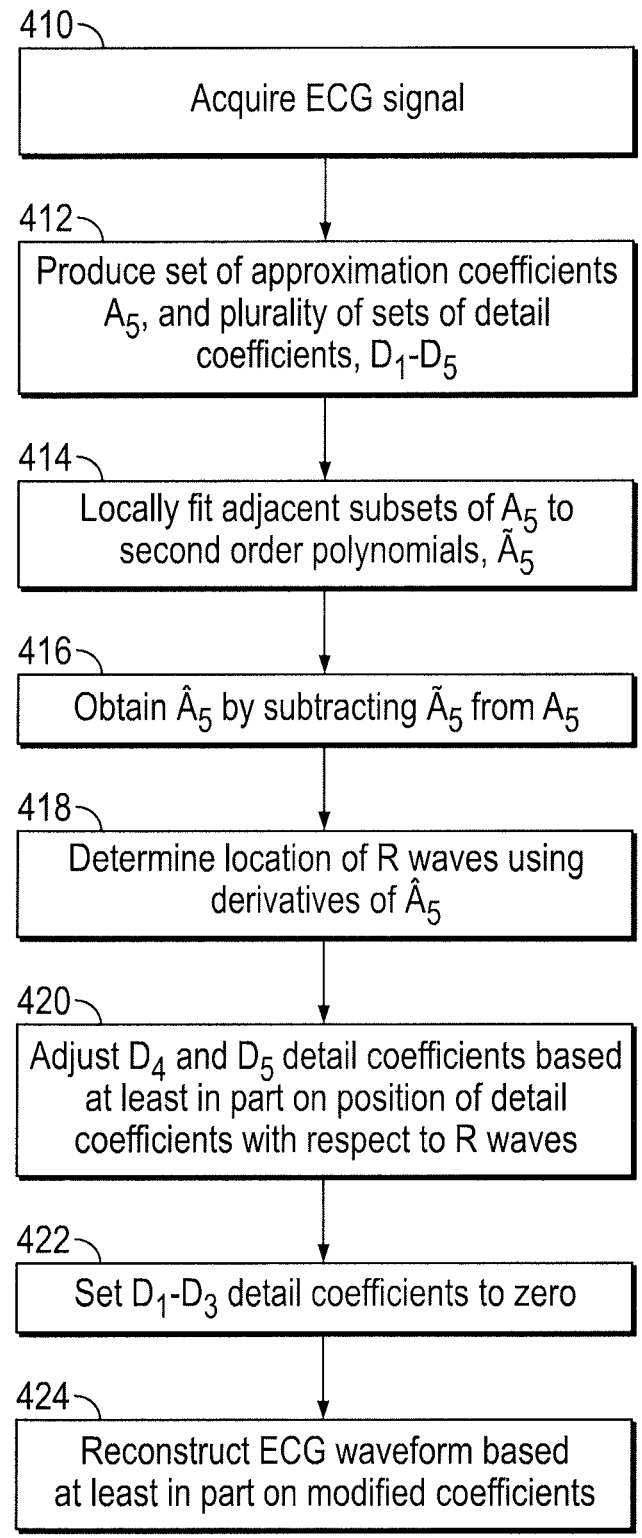
FIG. 7 shows a process flow diagram for one implementation of a method for processing an ECG signal to remove or reduce noise.

FIG. 7 illustrates a process flow diagram of for one implementation of a method for processing an ECG signal to remove or reduce noise. At block 410, an ECG signal that may contain EMG and/or motion artifacts is acquired. At block 412, wavelet decomposition is used to decompose the ECG signal from block 410. In some implementations, for example, the ECG signal is wavelet decomposed up to the $5^{th}$ order. In some implementations, however, the ECG signal can be decomposed to a lesser or greater order, e.g., up to the $n^{th}$ order, as described above. This decomposition can be achieved, for example, using a Biorthogonal 5.5 wavelet. Wavelet decomposition of the ECG signal up to the $5^{th}$ order will produce $5^{th}$ level approximation coefficients, $A_5$, and a plurality of sets of detail coefficients $D_1$-$D_5$. As described above, wavelet decomposition involves approximating a signal at progressively lower resolutions, with the difference in successive approximations defining a detail signal (e.g., detail coefficients). Thus, the approximation coefficients within set $A_5$ correspond to the value of the $5^{th}$ order approximation function (e.g., the approximated signal after decomposing up to the $5^{th}$ order) at discrete points, and the detail coefficients $D_1$-$D_5$ represent the difference between the approximation functions of successive orders.

At block 414, second order polynomials are locally fitted to the set of approximation coefficients $A_5$ to produce a set of locally fitted polynomial points $\tilde{A}_5$. In some implementations, the second order polynomials are locally fitted to the set of approximation coefficients such that the locally fitted points $\tilde{A}_5$ are generally fitted to the features of the motion artifact (as shown in FIG. 2), and not the features (e.g., the QRS wave complex) of the ECG signal (as shown in FIG. 1). This can be accomplished, for example, by locally fitting subsets that have a time period span greater than the time period of the ECG waveforms present in the data set, as discussed above. In some implementations, second order polynomials are fitted to the set of approximation coefficients using the algorithm described in detail above in the discussion of FIG. 5. At block 416, locally fitted second order polynomial points, $\tilde{A}_5$, are subtracted from the set of approximation coefficients, $A_5$, to obtain a set of modified approximation coefficients, $\hat{A}_5$.

At block 418, the location of R waves is determined based at least in part on the derivative of $\hat{A}_5$. In some implementations, the location of R waves can be determined by amplitude thresholding the derivative of $\hat{A}_5$. This method can be used because the R wave location should have the greatest derivative of any feature/wave of the ECG waveform. The specific amplitude threshold to use to determine the location of the R waves can be based at least in part on the mean and standard deviation of the derivative of $\hat{A}_5$. When the threshold is the mean plus 1.5 times the standard deviation, there will typically be one point in the remaining set of $\hat{A}_K$ for each R wave in the original signal. In some implementations, the location of R waves can be determined experimentally or using any other method known in the art.

At block 420, at least some of the $D_4$ and $D_5$ detail coefficients can be modified based at least in part on the time position of the detail coefficients with respect to the location of the R waves as determined in block 418. In some implementations, for example, detail coefficients in the $D_4$ and $D_5$ sets of detail coefficients are set to zero if they are more than a predetermined distance from the R waves based at least in part on the location of the R waves as determined in block 418. In some implementations, at least some of the $D_4$ and $D_5$ detail coefficients are position thresholded, e.g., set to zero based at least in part on the position of the detail coefficients with respect to the location of the R waves, substantially as described above in the discussion of FIG. 6. At block 422, the $D_1$-$D_3$ detail coefficients are set to zero.

At block 424, an ECG waveform is reconstructed based at least in part on the modified approximation coefficients obtained in block 416 and/or the modified detail coefficients obtained in blocks 420 and/or 422. In some implementations, the reconstructed ECG signal or waveform can have reduced or removed motion and/or EMG artifacts (e.g., the ECG signal can have reduced or removed noise) as compared to the original ECG signal acquired in block 410. It will be appreciated that the method and any combination of operations of the method described above can be performed substantially in real time.

Figure 8:
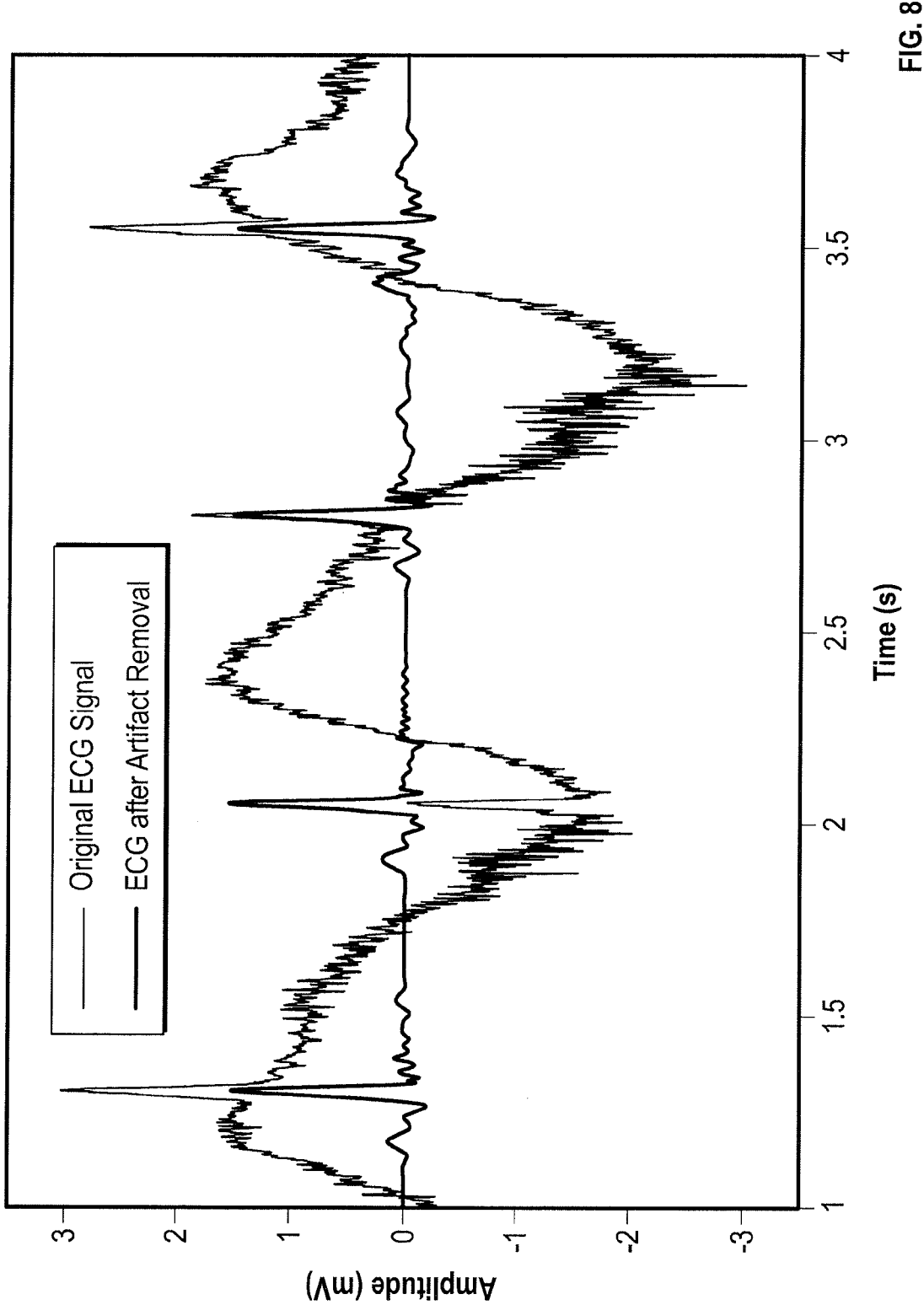
FIG. 8 shows an example of a comparison between an ECG signal corrupted by noise and the ECG signal after it has been processed to reduce the noise.

FIG. 8 shows the original signal of FIG. 2 and the FIG. 2 signal after it has been processed to reduce the noise. The original (corrupted) ECG signal has a large motion artifact, and high-frequency noise throughout the signal, characteristic of EMG artifacts. As demonstrated by this figure, the PQRST waves are easier to identify in the ECG signal after processing to remove or reduce the artifacts. It can be seen that baseline wander in the signal is also effectively removed with the LOWESS fitting procedure, which has proven to be difficult to accomplish with curve fitting techniques that attempt to fit the entire original signal span with a polynomial to remove motion artifacts.

Figure 3:
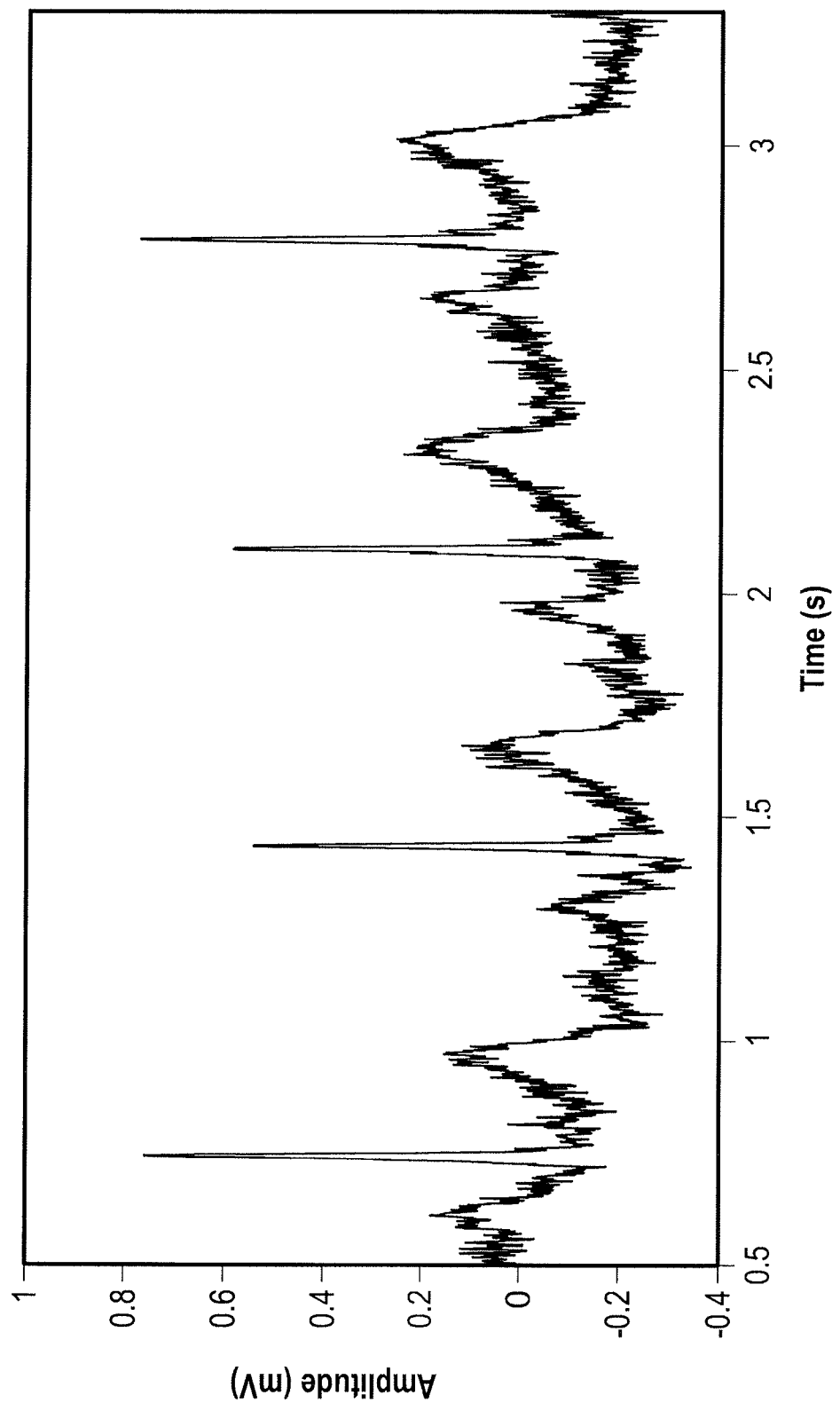
FIG. 3 shows an example of an ECG signal corrupted by EMG and motion artifacts.
Figure 9:
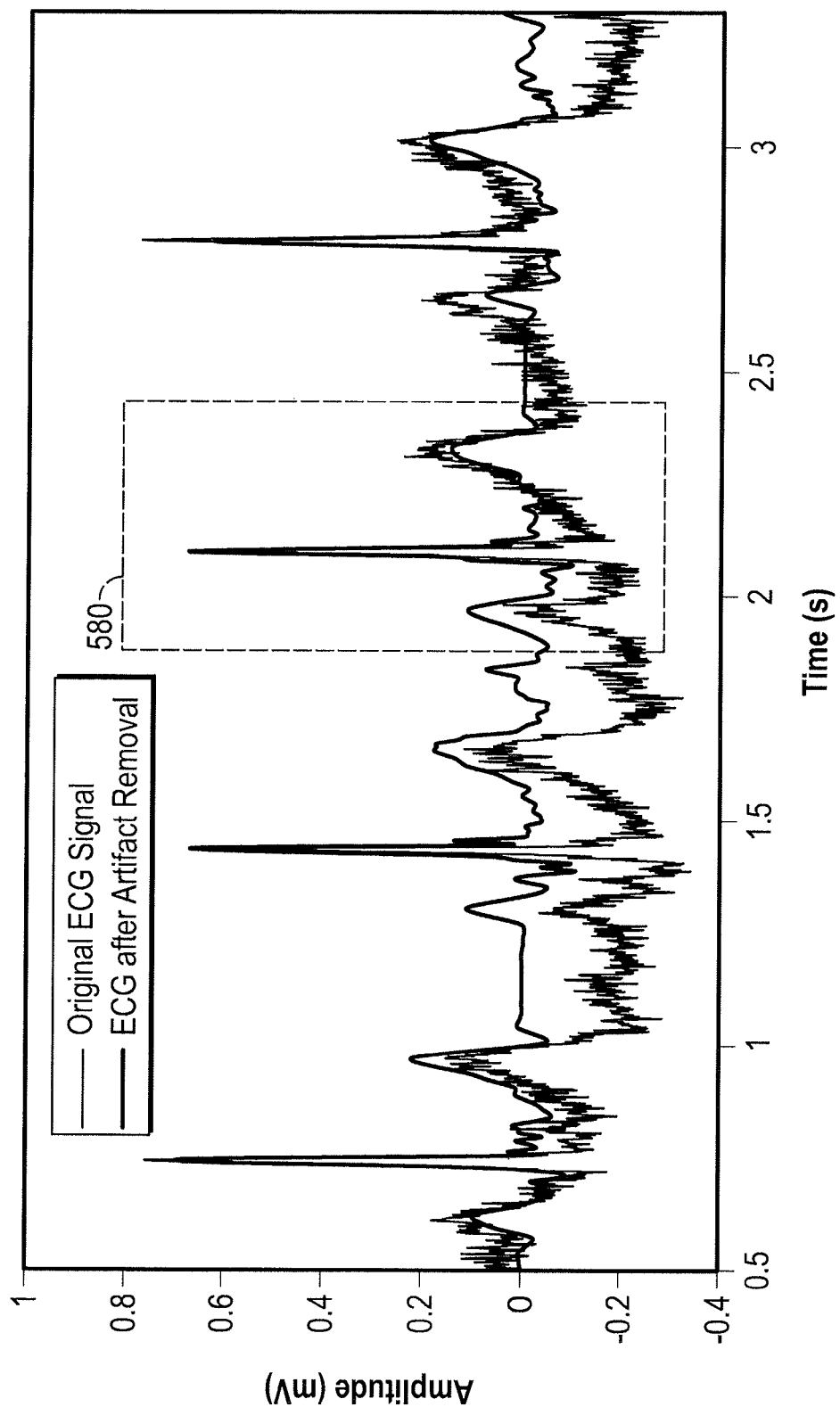
FIG. 9 shows an example of a comparison between an ECG signal corrupted by noise and the ECG signal after it has been processed to reduce the noise.

FIG. 9 shows the original signal of FIG. 3 with significant noise and the FIG. 3 signal after it has been processed to reduce the noise. As in FIG. 8, the P, Q, S and T waves of the ECG waveform 580 are difficult to identify in the ECG signal before processing to remove artifacts, and easier to identify in the ECG signal that has been processed to remove or reduce artifacts.

Figure 10:
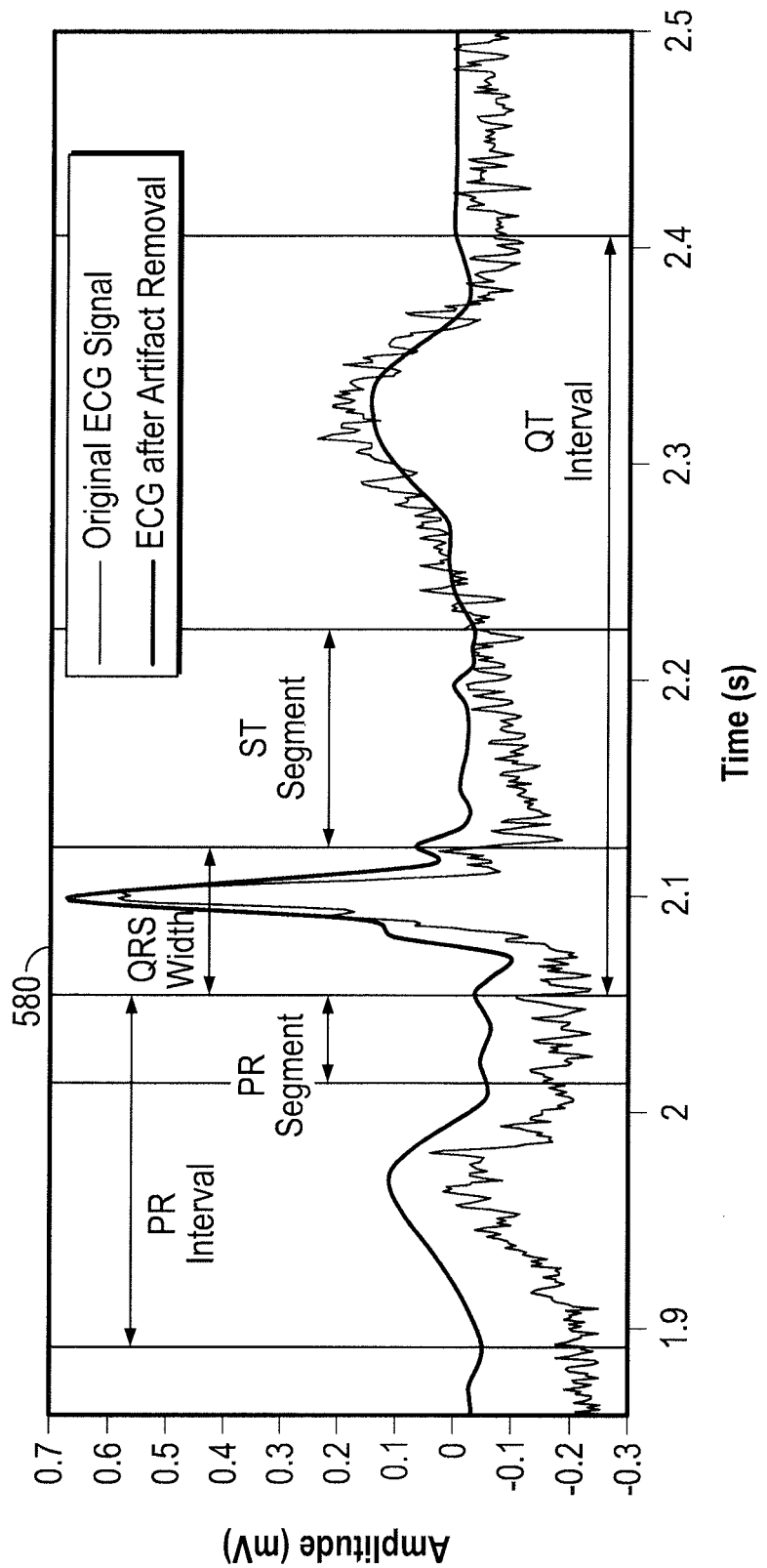
FIG. 10 shows an example of a comparison between an ECG signal corrupted by noise and the ECG signal after it has been processed to reduce the noise.

FIG. 10 shows block 580 of FIG. 9 in greater detail, showing a comparison between an ECG signal corrupted by noise and the ECG signal after it has been processed to reduce the noise. As in FIGS. 8 and 9, the P, Q, S and T waves of the ECG waveform 580 are difficult to identify in the ECG signal before processing to remove artifacts, and easier to identify in the ECG signal that has been processed to remove or reduce artifacts. FIG. 10 also illustrates the various time segments of ECG waveform 580, such as QRS width, that can be relevant in reading or analyzing an ECG signal.

Figure 11:
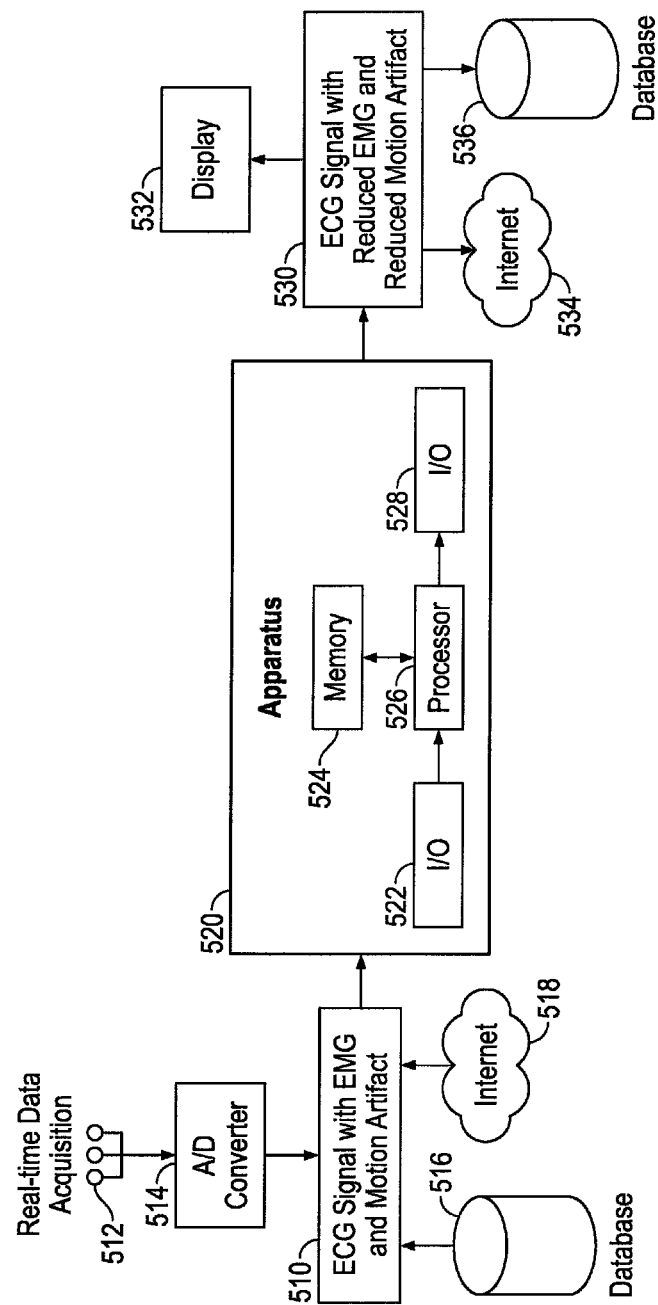
FIG. 11 shows a functional block diagram of one implementation of a system, apparatus or device for processing an ECG signal to reduce or remove noise in the ECG signal.

FIG. 11 illustrates a functional block diagram of one implementation of a system, apparatus or device for processing an ECG signal 510 to reduce or remove noise in the ECG signal 510. In some implementations, an ECG signal 510 having EMG and/or motion artifacts can be acquired through real-time data acquisition 512, for example one or more electrodes mounted on a subject. The signal acquired through real-time data acquisition can be transmitted to an A/D converter 514 which can process the signal and produce, for example, time domain samples of the signal. The ECG signal 510 can also be acquired from a database 516, from the Internet 518, or from any other source or storage medium known in the art.

The ECG signal is then transmitted or routed to apparatus 520, where it is received by I/O (input/output) module of device 522. I/O device 522 can be, for example, an antenna, a data port, or any other device known in the art. The signal can be transmitted or routed to processor 526 configured to process the ECG signal to remove or reduce the EMG and/or motion artifacts. As described below, processor 526 can be any variety or combination of processors known in the art, including, for example, a general purpose processor, a digital signal processor, or an application specific integrated circuit. Processor 526 may be configured to perform any one or any combination of the processing operations detailed above, including wavelet decomposing the ECG signal 510 to produce a set of approximation coefficients and a plurality of sets of detail coefficients. Processor 526 may be further configured to modify the approximation and/or detail coefficients. In some implementations, processor 526 may be configured to modify the coefficients using any one or any combination of the processing operations detailed above, including locally fitting second order polynomials to the approximation coefficients to produce second order polynomial points, subtracting the locally fitted second order polynomial points from the approximation coefficients to obtain modified approximation coefficients, determining the location of R waves based at least in part on the derivative of the modified approximation coefficients, setting some sets of detail coefficients to zero, and/or position thresholding some detail coefficients based at least in part on the position of the detail coefficients with respect to R waves of the ECG signal to obtain modified detail coefficients. Processor 526 may also be configured to reconstruct an ECG signal 530 with reduced or removed motion and/or EMG artifacts from the modified approximation coefficients and/or modified detail coefficients. If the system is implemented as software, the processor may be programmed to perform these functions using instructions or code (e.g., in the form of modules) that may be stored in memory 524. Memory 524 may be any storage media accessible by a computer. Before, during, and/or after processing, the ECG signal and any portion thereof, including, for example, the sets of approximation coefficients or modified approximation coefficients, may be transmitted or routed to and stored in memory 524, and may be retrieved from memory 524 for use by processor 526. After processing of the ECG signal 510 by processor 524, the processed ECG signal may be transmitted or routed to I/O module or device 528.

After processing, depending on the operations or methods performed by processor 524, the ECG signal 510 may be an ECG signal with reduced or removed EMG and/or motion artifacts 530. In some implementations, ECG signal with reduced EMG and/or reduced motion artifact 530 can then be transmitted or routed to a display 532 configured to display the ECG signal 530, so that it can be read and/or analyzed. ECG signal 530 may also be transmitted or routed to the Internet 534 or to database 536 for storage and/or subsequent transmission. It will be appreciated that any portion of the system, apparatus, or device illustrated in FIG. 11 can be configured to perform any function or task detailed above substantially in real time, e.g., a signal is processed when it is received from database 516, the Internet 518, or as it is acquired through real-time data acquisition 512.

Figure 12A:
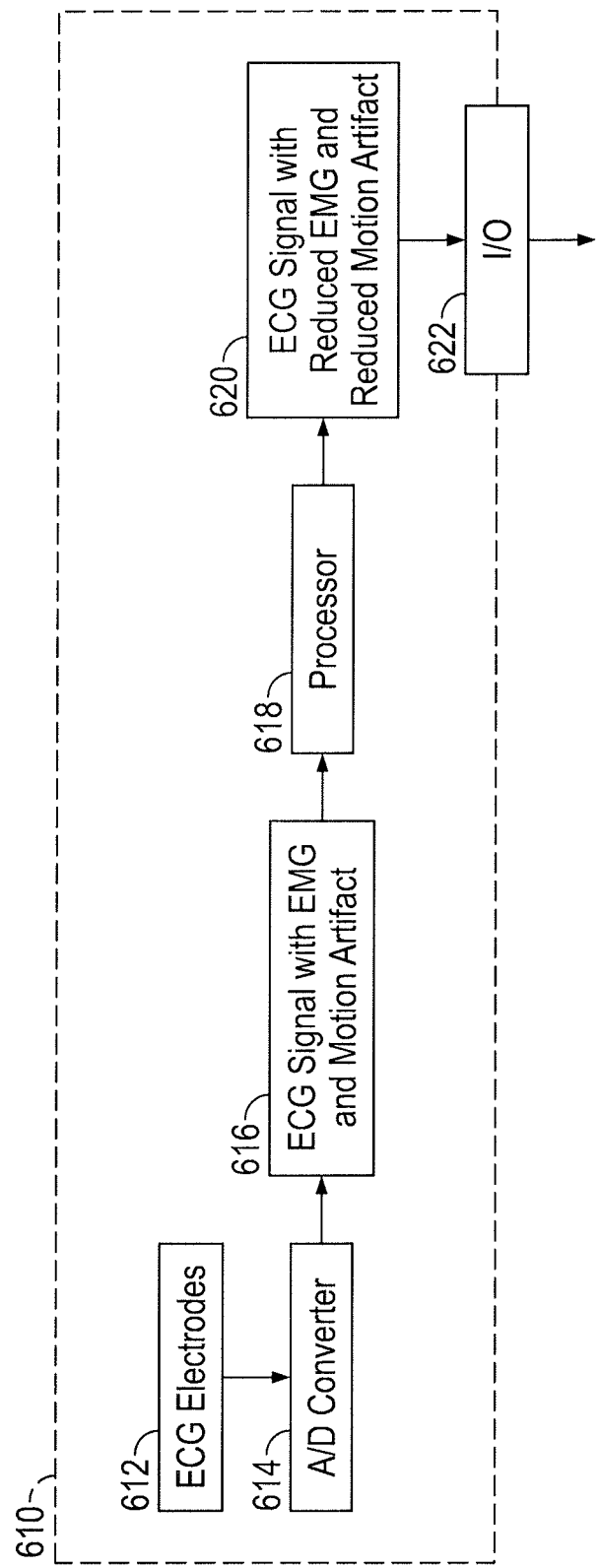
FIG. 12A shows a functional block diagram of one implementation of a system, apparatus or device for processing an ECG signal to remove or reduce noise in the ECG signal.

FIG. 12A shows a functional block diagram of one implementation of a system, apparatus or device 610 (hereafter "device 610") for processing an ECG signal to remove or reduce noise in the ECG signal. Device 610 can include ECG electrodes 612, which can be used to acquire an ECG signal from a subject. ECG electrodes 612 can be mounted on a subject, for example, using adhesive on one surface of the electrodes 612, in order to acquire a signal. Electrodes 612 can be mounted, for example, on the skin of a subject near an area external the heart of the subject. The signal acquired by electrodes 612 can then be transmitted or routed to A/D converter 614, which can be configured to produce time domain samples of the signal acquired by the electrodes 612. The time domain samples produced by A/D converter 614 are a representation of the ECG signal having EMG and/or motion artifacts 616 as acquired by electrodes 612. ECG signal with EMG and/or motion artifacts 616 can be transmitted to processor 618 for processing to remove or reduce the EMG and/or motion artifacts.

As described below, processor 618 can be any variety or combination of processors known in the art, including, for example, a general purpose processor, a digital signal processor, or an application specific integrated circuit. Processor 618 may be configured to perform any one or any combination of the processing operations detailed above, including wavelet decomposing the ECG signal 616 to produce a set of approximation coefficients and a plurality of sets of detail coefficients. Processor 618 may be further configured to modify the approximation and/or detail coefficients. In some implementations, processor 618 may be configured to modify the coefficients using any one or any combination of the processing operations detailed above, including locally fitting second order polynomials to the approximation coefficients to produce second order polynomial points, subtracting the locally fitted second order polynomial points from the approximation coefficients to obtain modified approximation coefficients, determining the location of R waves based at least in part on the derivative of the modified approximation coefficients, setting some sets of detail coefficients to zero, and/or position thresholding some detail coefficients based at least in part on the position of the detail coefficients with respect to R waves of the ECG signal to obtain modified detail coefficients. Processor 618 may also be configured to reconstruct an ECG signal 620 with reduced or removed motion and/or EMG artifacts from the modified approximation coefficients and/or modified detail coefficients. If the system is implemented as software, the processor may be programmed to perform these functions using instructions or code (e.g., in the form of modules) that may be stored in memory accessible by processor 618. The processed ECG signal with reduced EMG and/or motion artifacts 620 can then be transmitted to I/O module or device 622. I/O 622 can then transmit ECG signal 620 to any device, apparatus, or storage configured to receive ECG signal 620 for purposes of displaying, storing, transmitting, or further processing of ECG signal 620. It will be appreciated that device 610 is configured to perform the functions and tasks detailed above substantially in real time.

Figure 12B:
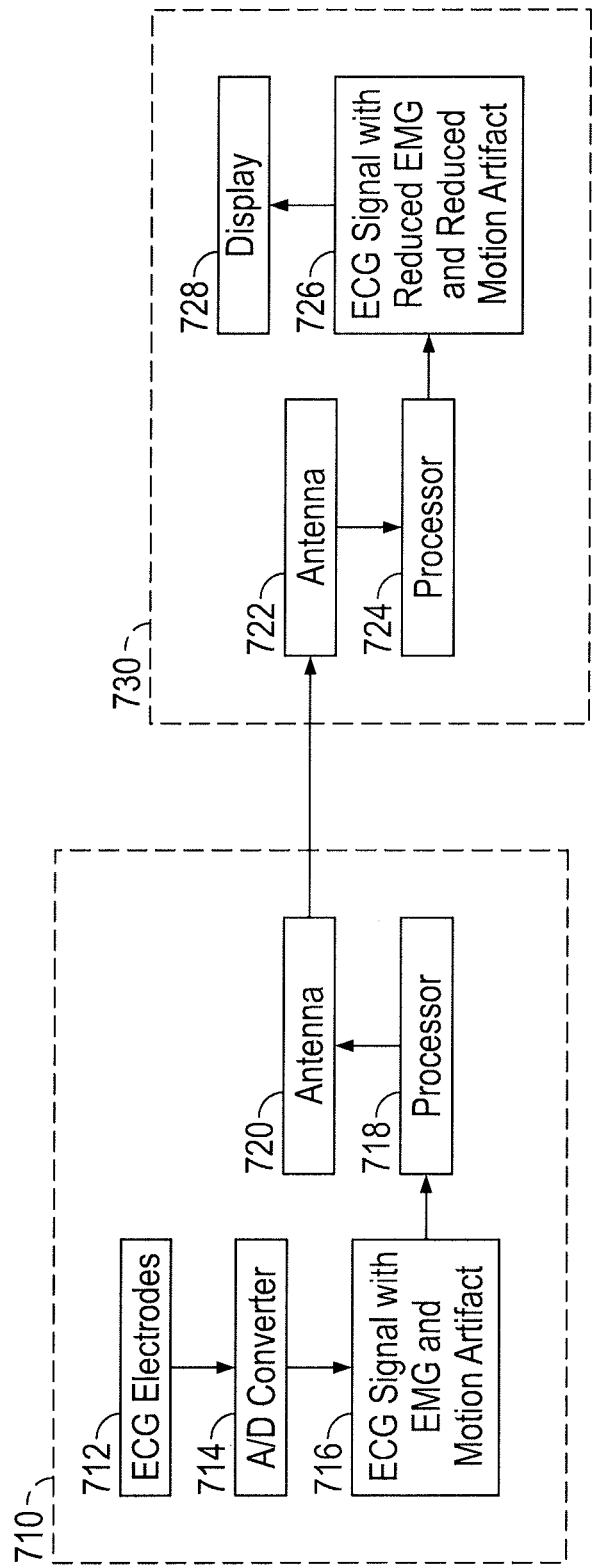
FIG. 12B shows a functional block diagram of one implementation of a system, apparatus or device for processing an ECG signal to remove or reduce noise in the ECG signal.

FIG. 12B shows a functional block diagram of one implementation of a system, apparatus or device for processing an ECG signal to remove or reduce noise in the ECG signal. In some implementations, the system, apparatus or device of FIG. 12B can be an ambulatory ECG monitoring system. The system can include an acquisition system, apparatus or device 710 (hereinafter "device 710"), such as, for example, a patch ECG monitor. The patch ECG monitor can include ECG electrodes 712, an A/D converter 714, a processor or signal processing circuitry 718, and an antenna 720. The ECG electrodes 712 can be mounted on a subject, e.g., on the skin of a subject using adhesive on one side of the electrodes, and can be configured to acquire an ECG signal (e.g., raw sampled data points) from the subject. The signal acquired by the electrodes can then be routed to the A/D converter, which is configured to produce time domain samples of the ECG signal with EMG and/or motion artifacts 716. ECG signal 716 can be sent to processor or signal processing circuitry 718 configured to process the signal acquired by the electrodes.

As described below, processor 718 can be any variety or combination of processors known in the art, including, for example, a general purpose processor, a digital signal processor, or an application specific integrated circuit. Processor 718 may be configured to perform any one or any combination of the processing operations detailed above, including wavelet decomposing the ECG signal 716 to produce a set of approximation coefficients and a plurality of sets of detail coefficients. Processor 718 may be further configured to modify the approximation and/or detail coefficients. In some implementations, processor 718 may be configured to modify the coefficients using any one or any combination of the processing operations detailed above, including locally fitting second order polynomials to the approximation coefficients to produce second order polynomial points, subtracting the locally fitted second order polynomial points from the approximation coefficients to obtain modified approximation coefficients, determining the location of R waves based at least in part on the derivative of the modified approximation coefficients, setting some sets of detail coefficients to zero, and/or position thresholding some detail coefficients based at least in part on the position of the detail coefficients with respect to R waves of the ECG signal to obtain modified detail coefficients. Processor 718 may also be configured to reconstruct an ECG signal 726 with reduced or removed motion and/or EMG artifacts from the modified approximation coefficients and/or modified detail coefficients. Alternatively, processor 718 can configured to process or compress ECG signal 716 to be transmitted via antenna 720 to another system, apparatus or device 730 to perform further processing of the signal 716.

The processed ECG signal 716, or a compressed version thereof, can be transmitted wirelessly via antenna 720 to a system, apparatus or device 730 (hereafter "device 730"). Device 730 can be a mobile device, such as, for example, a cell phone, tablet, or other portable electronic system, which receives the data via an antenna 722 and routes the data to processor or signal processing circuitry 724. Processor 724 can be configured to perform any combination or all of the processing operations of the novel algorithm detailed above to reduce or remove EMG and/or motion artifacts from the ECG signal 716 to produce an ECG signal with reduced or removed EMG and/or motion artifacts 726. Device 730 may include display 728 configured to display the ECG signal 726. Display 728 may be configured to manipulate ECG signal 726 with a keypad/touchscreen on the mobile device. Device 730 may also be configured to transmit the waveform or a compressed version thereof to an external network, such as the Internet, for storage, review by a physical, etc.

It will be appreciated that the components of the system, apparatus or devices illustrated in FIG. 12B need not be mounted together on the same physical substrate, but could be split up in a variety of ways to perform the previously described operations and functions of devices 710 and 730. It will also be appreciated that devices 710 and 730 are configured to perform the functions and tasks detailed above substantially in real time.

The various illustrative logic, logical blocks, modules, and algorithm operations described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and operations described above. Whether such functionality is implemented in hardware of software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any convention processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. In some implementations, particular operations and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, e.g., one or more modules of computer program instructions, encoded on a computer storage media for execution by, or to control the operation of, data processing apparatus.

If implemented in software, the functions may be stored on or transmitted over as one or more instructions or code on a computer-readable medium. The operations of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk and blue-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claim combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one or more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally by integrated together in a single software product or packaged in multiple software products. Additionally, other implementations are within the scope of the following claims. In some cases, the actions recited in the claims can be performed in a different order and still achieve desirable results.

What is claimed is:

1. A computer implemented method of reducing noise in an ECG signal, the method comprising:
   wavelet decomposing an ECG waveform with a processor to produce a set of approximation coefficients and a plurality of sets of detail coefficients; and
   modifying the set of approximation coefficients with a processor to reduce noise attributable to subject motion during acquisition of the ECG waveform to produce a set of modified approximation coefficients,
   wherein the modifying the set of approximation coefficients comprises locally fitting adjacent subsets of the approximation coefficients to second order polynomials.

2. The method of claim 1, further comprising adjusting the set of approximation coefficients by subtracting corresponding values of the second order polynomials to produce a set of modified approximation coefficients.

3. The method of claim 1, further comprising setting the values of $D_1$, $D_2$ and $D_3$ sets of detail coefficients to zero.

4. The method of any one of claim 1, 2, or 3, further comprising position thresholding the detail coefficients of the decomposition based at least in part on the position of the detail coefficients with respect to an R wave of the ECG signal to reduce noise attributable to EMG signals in the ECG waveform.

5. The method of claim 4, wherein the position thresholded detail coefficients comprise D4 and D5 sets of detail coefficients.

6. The method of claim 2, further comprising:
   determining the location of R waves of the ECG waveform based at least in part on the derivatives of the modified approximation coefficients; and
   position thresholding detail coefficients of the decomposition based at least in part on the position of the detail coefficients with respect to the R waves of the ECG signal to reduce noise attributable to EMG signals in the ECG waveform.

7. The method of any one of claim 1, 2, 3, 5, or 6, wherein the set of approximation coefficients comprise 5th level approximation coefficients.

8. An ECG signal processing apparatus, the apparatus comprising:
   a processor configured to:
      wavelet decompose the ECG waveform to produce a set of approximation coefficients and a plurality of sets of detail coefficients; and
      modify the set of approximation coefficients to reduce noise attributable to subject motion during acquisition of the ECG waveform to produce a set of modified approximation coefficients,
   wherein the processor is configured to modify the set of approximation coefficients by locally fitting adjacent subsets of the approximation coefficients to second order polynomials.

9. The apparatus of claim 8, wherein the processor is further configured to position threshold detail coefficients of the decomposition based at least in part on the position of the detail coefficients with respect to R waves of the ECG signal to reduce noise attributable to EMG signals in the ECG waveform.

10. The apparatus of claim 8 or 9, wherein the apparatus comprises ECG electrodes, an A/D converter, and an antenna configured for mounting on the body of a subject.

11. A computer implemented method of reducing noise in an ECG signal, the method comprising:
wavelet decomposing an ECG waveform with a processor to produce a set of approximation coefficients and a plurality of sets of detail coefficients; and
position thresholding detail coefficients of the decomposition based at least in part on the position in time of the detail coefficients with respect to R waves of the ECG signal to reduce noise attributable to EMG signals in the ECG waveform.

12. The method of claim 11, further comprising modifying the set of approximation coefficients with a processor to reduce noise attributable to subject motion during acquisition of the ECG waveform.

13. The method of claim 12, wherein modifying the set of approximation coefficients comprises locally fitting adjacent subsets of the approximation coefficients to second order polynomials.

14. The method of claim 11, wherein the position thresholding detail coefficients of the decomposition comprises zeroing the one or more detail coefficients that are more than a predetermined distance in time from the R waves.

15. An ECG signal processing apparatus, the apparatus comprising:
a processor configured to:
wavelet decompose the ECG waveform to produce a set of approximation coefficients and a plurality of sets of detail coefficients; and
position threshold detail coefficients of the decomposition based at least in part on the position in time of the detail coefficients with respect to R waves of the ECG signal to reduce noise attributable to EMG signals in the ECG waveform.

16. The apparatus of claim 15, wherein the processor is further configured to modify the approximation coefficients to reduce noise attributable to subject motion during acquisition of the ECG waveform.

17. The apparatus of claim 16, wherein the processor is further configured to modify the approximation coefficients by locally fitting adjacent subsets of the approximation coefficients to second order polynomials.

18. The apparatus of claim 17, wherein the processor is further configured to produce a set of modified approximation coefficients by adjusting the set of approximation coefficients by subtracting corresponding values of the second order polynomials.

19. The apparatus of claim 18, wherein the processor is further configured to determine the location of R waves of the ECG signal based at least in part on the derivatives of the modified set of approximation coefficients.

20. The apparatus of any one of claims 15-19, wherein the apparatus comprises ECG electrodes, an A/D converter, and an antenna configured for mounting on the body of a subject.

21. The apparatus of claim 15, wherein the processor is configured to position threshold detail coefficients of the decomposition by zeroing the one or more detail coefficients that are more than a predetermined distance in time from the R waves.

22. A computer implemented method of processing an ECG signal, the method comprising:
wavelet decomposing an ECG waveform with a processor to produce a set of approximation coefficients and a plurality of sets of detail coefficients;
locally fitting with a processor adjacent subsets of the approximation coefficients to second order polynomials;
adjusting the approximation coefficients using the second order polynomials to produce a set of modified approximation coefficients;
determining the location of R waves of the ECG signal based at least in part on the derivatives of the set of modified approximation coefficients; and
position thresholding with a processor detail coefficients of the decomposition by setting some of the detail coefficients to zero based at least in part on the position of the detail coefficients with respect to the R waves of the ECG signal to produce a plurality of sets of modified detail coefficients.

23. The method of claim 22, further comprising reconstructing the ECG waveform with a processor from at least a portion of the set of modified approximation coefficients and the plurality of sets of modified detail coefficients.

24. The method of claim 22 or 23, wherein the set of approximation coefficients comprise 5th level approximation coefficients.

25. The method of claim 22, further comprising setting the values of $D_1$, $D_2$ and $D_3$ sets of detail coefficients to zero.

26. The method of claim 22 or 25, wherein the position thresholded detail coefficients comprise $D_4$ and $D_5$ sets of detail coefficients.

27. An apparatus for reducing noise in an ECG signal, the apparatus comprising:
a processor configured to:
wavelet decompose an ECG waveform to produce a set of approximation coefficients and a plurality of sets of detail coefficients;
locally fit adjacent subsets of the approximation coefficients to second order polynomials;
adjust the approximation coefficients using the second order polynomials to produce a set of modified approximation coefficients;
determine the location of R waves of the ECG signal based at least in part on the derivatives of the set of modified approximation coefficients; and
position threshold detail coefficients of the decomposition based at least in part on the position of the detail coefficients with respect to the R waves of the ECG signal to produce a plurality of sets of modified detail coefficients.

28. The apparatus of claim 27, wherein the processor is further configured to reconstruct the ECG waveform from at least a portion of the set of modified approximation coefficients and the plurality of sets of modified detail coefficients.

29. The apparatus of claim 27, wherein the apparatus comprises ECG electrodes, an A/D converter, and an antenna configured for mounting on the body of a subject.

30. A device for processing an ECG signal, comprising:
means for wavelet decomposing an ECG waveform to produce a set of approximation coefficients and a plurality of sets of detail coefficients;
means for locally fitting adjacent subsets of the approximation coefficients to second order polynomials;
means for adjusting the approximation coefficients using the second order polynomials to produce a set of modified approximation coefficients;
means for determining the location of R waves of the ECG signal based at least in part on the derivatives of the set of modified approximation coefficients; and
means for position thresholding detail coefficients of the decomposition by setting some of the detail to coefficients to zero based at least in part on the position of the detail coefficients with respect to the R waves of the ECG signal to produce a plurality of sets of modified detail coefficients.

31. The device of claim 30, further comprising means for reconstructing the ECG waveform from at least a portion of the set of modified approximation coefficients and the plurality of sets of modified detail coefficients.

32. The device of claim 30 or 31, wherein the approximation coefficients comprise 5th level approximation coefficients.

33. The device of claim 30 or 31, wherein the position thresholded detail coefficients comprise $D_4$ and $D_5$ sets of detail coefficients.

* * * * *